United States Patent [19]

Manis et al.

[11] 4,401,761
[45] Aug. 30, 1983

[54] PROCESS FOR STABILIZING PLASMIDS BY DELETION OF DNA

[75] Inventors: Jack J. Manis, Portage; Sarah K. Highlander, Kalamazoo, both of Mich.

[73] Assignee: The Upjohn Company, Kalamazoo, Mich.

[21] Appl. No.: 352,499

[22] Filed: Feb. 25, 1982

Related U.S. Application Data

[62] Division of Ser. No. 228,240, Jan. 26, 1981, Pat. No. 4,338,400.

[51] Int. Cl.[3] .................. C12N 15/00; C12P 21/02; C12P 21/00; C12N 1/20; C12N 1/00
[52] U.S. Cl. .................................. 435/172; 435/70; 435/68; 435/253; 435/317
[58] Field of Search .................. 435/68, 317, 172, 253

[56] References Cited

PUBLICATIONS

Timmis; in *Plasmids of Medical, Environmental and Commercial Importance*, Timmis et al., (ed.), Elsevier/North Holland, 1979, pp. 13–22.
Thomas et al., in *Plasmids of Medical, Environmental and Commercial Importance*, Timmis et al., (ed.), Elsevier/North Holland, 1979, pp. 375–385.
Thompson, C. J., et al., "DNA Cloning in Streptomyces; Resistance Genes from Antibiotic-Producing Species." Nature 286, 525–527.
Suarez, J. E. et al., "DNA Cloning in Streptomyces . . ." Nature 286, 527–529.
Bibb, M. et al., "A DNA Cloning System for Interspecies Gene Transfer in Antibiotic-Producing Streptomyces." Nature 284, 526–531.

*Primary Examiner*—Alvin E. Tanenholtz
*Assistant Examiner*—James Martinell
*Attorney, Agent, or Firm*—Roman Saliwanchik

[57] ABSTRACT

Novel chemical compounds, recombinant plasmids pUC1026 and pUC1027, which are obtained by covalent linkage of the *E. coli* plasmid pBR322 to the *Streptomyces espinosus* plasmid pUC6. These plasmids are produced by a novel process which can be used to stabilize unstable potential plasmid vectors. These plasmids are useful as cloning vehicles in recombinant DNA work. For example, using DNA methodology, a desired gene, for example, the insulin gene, can be inserted into the plasmids and the resulting plasmids can then be transformed into a suitable host microbe which, upon culturing, produces the desired insulin. The stabilization process disclosed herein can be used to make other stable plasmids.

1 Claim, 6 Drawing Figures

PROCESS FOR STABILIZING PLASMIDS BY DELETION OF DNA

This is a division of application Ser. No. 228,240, filed Jan. 26, 1981, now U.S. Pat. No. 4,338,400.

BACKGROUND OF THE INVENTION

The development of plasmid vectors useful for recombinant DNA genetics among microorganisms is well known. The editorial in Science, Vol. 196, April, 1977, gives a good summary of DNA research. This editorial is accompanied by a number of supporting papers in the same issue of Science.

Similar DNA work is currently being done on industrially important microorganisms of the genus Streptomyces. [Bibb, M. J., Ward, J. M., and Hopwood, D. A. 1978. "Transformation of plasmid DNA into Streptomyces at high frequency." Nature 274, 398-400.] Though plasmid DNA's have been described in several streptomycetes [Huber, M. L. B. and Godfrey, O. 1978. "A general method for lysis of Streptomyces species." Can. J. Microbiol. 24, 631-632.] [Schrempf, H., Bujard, H., Hopwood, D. A. and Goebel, W. 1975. "Isolation of covalently closed circular deoxyribonucleic acid from *Streptomyces coelicolor* A3(2)." J. Bacteriol. 121, 416-421.] [Umezawa, H. 1977. "Microbial secondary metabolites with potential use in cancer treatment (Plasmid involvement in biosynthesis and compounds)." Biomedicine 26, 236-249.], [Malik, V. S. 1977. "Preparative Method for the isolation of super-coiled DNA from a chloramphenicol producing streptomycete." J. Antibiotics 30, 897-899], only one streptomycete plasmid has been physically isolated and extensively characterized in the literature [Schrempf, supra], [Thompson, C. J., Ward, J. M., and Hopwood, D. A. 1980. "DNA cloning in Streptomyces: resistance genes from antibiotic-producing species." Nature 286, 525-527.] [Saurez,, J. E. and Chater, K. F. 1980. "DNA cloning in Streptomyces: a bifunctional replicon comprising pBR322 inserted into a Streptomyces phage." Nature 286, 527-529.] See also [Bibb, M., Schottel, J. L., and Cohen, S. N. 1980. "A DNA cloning system for interspecies gene transfer in antibiotic-producing Streptomyces." Nature 284, 526-531.] The existence of other plasmids in the genus Streptomyces has been inferred from reported genetic data as follows:

(1) Akagawa, H., Okanishi, M. and Umezawa, H. 1975. "A plasmid involved in chloramphenicol production in *Streptomyces venezuelae*: Evidence from genetic mapping." J. Gen. Microbiol. 90, 336-346.

(2) Freeman, R. F. and Hopwood, D. A. 1978. "Unstable naturally occurring resistance to antibiotics in Streptomyces." J. Gen. Microbiol. 106, 377-381.

(3) Friend, E. J., Warren, M. and Hopwood, D. A. 1978. "Genetic evidence for a plasmid controlling fertility in an industrial strain of *Streptomyces rimosus*." J. Gen. Microbiol. 106, 201-206.

(4) Hopwood, D. A. and Wright, H. M. 1973. "A plasmid of *Streptomyces coelicolor* carrying a chromosomal locus and its inter-specific transfer." J. Gen. microbiol. 79, 331-342.

(5) Hotta, K., Okami, Y. and Umezawa, H. 1977. "Elimination of the ability of a kanamycin-producing strain to biosynthesize deoxystreptamine moiety by acriflavine." J. Antibiotics 30, 1146-1149.

(6) Kirby, R., Wright, H. M. and Hopwood, D. A. 1975. "Plasmid-determined antibiotic synthesis and resistance in *Streptomyces coelicolor*." Nature 254, 265-267.

(7) Kirby, R. and Hopwood, D. A. 1977. "Genetic determination of methylenomycin synthesis by the SCPI plasmid of *Streptomyces coelicolor* A3(2)." J. Gen. Microbiol. 98, 239-252.

(8) Okanishi, M., Ohta, T. and Umezawa, H. 1969. "Possible control of formation of aerial mycleium and antibiotic production in Streptomyces by episomic factors." J. Antibiotics 33, 45-47.

Plasmid pUC6 was isolated from *Streptomyces espinosus* biotype 23724a, NRRL 11439.

Plasmid pBR322 is a well known plasmid which can be obtained from *E. coli* RR1, NRRL B-12014. The restriction endonuclease map for pBR322 is published [Sutcliff, J. G. "pBR322 restriction map derived from the DNA sequence: accurate DNA size markers up to 4361 nucleotide pairs long." Nucleic Acids Research 5, 2721-2728, 1978]. This map is incorporated herein by reference to the above publication.

BRIEF SUMMARY OF THE INVENTION

Plasmids pUC1026 and pUC1027 are obtained by the in vitro covalent linkage of the *E. coli* plasmid pBR322 to portions of the *S. espinosus* plasmid pUC6. These plasmids lack a locus contained in the pUC6 genome which causes the genetic instability of other dual vector pUC6:pBR322 recombinant plasmids in *E. coli* hosts. The subject invention comprises these novel stable plasmids, and also a process for stabilizing an unstable potential plasmid vector in a naive host. A naive host, as used herein, is a host which has never contained the said potential plasmid vector. The identification of such a plasmid born instability locus is an important factor in the development of vector systems using streptomycete plasmids alone or in combination with plasmids and/or viruses from other organisms. Though the vector system exemplified herein is specifically to a dual vector, i.e., pUC6:pBR322, it is within the concept of this invention that single plasmid vectors exhibiting instability in a host can likewise be stabilized by elimination of an instability locus. Such elimination can be by deletion of the particular locus, mutation, and the like.

REFERENCE TO THE DRAWINGS

The maps are constructed on the bases of plasmids pUC1026 and pUC1027 having a molecular weight of ca. 5.4 and 5.6 megadaltons, respectively, or a molecular length of ca. 8.1 and 8.5 kilobases, respectively. The restriction endonuclease abbreviations are all standard and well known.

pUC1026 and pUC1027 can be used to create recombinant plasmids which can be introduced into host microbes by transformation. The process of creating recombinant plasmids is well known in the art. Such a process comprises cleaving the isolated vector plasmid at a specific site(s) by means of a restriction endonuclease, for example, BglII, XhoI, and the like. The plasmid, which is a circular DNA molecule, is thus converted into a linear DNA molecule or molecular fragments by the enzyme which cuts the two DNA strands at a specific site(s). Other non-vector DNA is similarly cleaved with the same enzyme. Upon mixing the linear vector or portions thereof and non-vector DNA's, their single-stranded or blunt ends can pair with each other and in the presence of a second enzyme known as polynucleotide ligase can be covalently joined to form a single circle of DNA.

The above procedure also can be used to insert a length of DNA from a higher animal into pUC1026 or pUC1027. For example, the DNA which codes for ribosomal RNA in the frog can be mixed with pUC1026 DNA that has been cleaved. The resulting circular DNA molecules consist of plasmid pUC1026 with an inserted length of frog rDNA.

The recombinant plasmids containing a desired genetic element, prepared by using pUC1026 or pUC1027, can be introduced into a host organism for expression. Examples of valuable genes which can be inserted into host organisms by the above described process are genes coding for somatostatin, rat proinsulin, interferon, and proteases.

The usefulness of plasmids pUC1026 and pUC1027 is derived from their capacity to function as plasmid vectors in industrially important microorganisms, e.g., Streptomyces. Also, pUC1026 and pUC1027 are especially useful because of their single restriction sites. Hence, cloning of genetic information from Streptomyces into pUC1026 or pUC1027 provides a means of increasing the production of commercially important products from these organisms, e.g., antibiotics.

This approach is compared to the concept of cloning genes for antibiotic production into the well characterized *Escherichia coli* K-12 host-vector system. The *E. coli* system has the disadvantage that it has been found that genes from some Gram-positive organisms, e.g., Bacillus, do not express well in the Gram-negative *E. coli* host. Similarly, reports have appeared that indicate Streptomyces DNA is not expressed in *E. coli*. Likewise, plasmids from Gram-negative organisms are not maintained in Gram-positive hosts, and Gram-negative genetic information is either expressed poorly or not at all in Gram-positive hosts. This clearly argues for the advantage of a Gram-positive host-vector system and argues the usefulness of plasmid pUC1026 or pUC1027 in such a system.

In general, the use of a host-vector system to produce a product foreign to that host requires the introduction of the genes for the entire biosynthetic pathway of the product to the new host. As discussed above, this may lead to problems of genetic expression, but may also generate new and/or increased problems in the fermentation of the microorganisms and in the extraction and purification of the product. A perhaps more useful approach is to introduce a plasmid vector into a host which normally produces the product and clone onto that plasmid the genes for biosynthesis of the product. At the very least, problems of fermentation and product extraction and purification should be minimized. Additionally, in this cloning system it may not be necessary to clone and amplify all the genes of the biosynthetic pathway, but rather it may be necessary only to clone regulatory genes or genes coding for the enzymes that are rate limiting in product biosynthesis. Since pUC1026 and pUC1027 are recombinant plasmids which contain DNA from organisms that do not normally exchange genetic information, they can be used to clone DNA sequences in *E. coli* or within the genera of Streptomyces and Micromonospora, as well as within other microbes.

DETAILED DESCRIPTION OF THE INVENTION

The Microorganisms and Plasmids

The following microorganisms are available from the permanent collection of the Northern Regional Research Laboratory, U.S. Department of Agriculture, Peoria, Ill., U.S.A.

NRRL B-12110—*E. coli* CSH50
NRRL B-11439—*S. espinosus* biotype 23724a
NRRL B-12014—*E. coli* RR1 (pBR322)
NRRL B-12107—*E. coli* CSH50 (pUC1013)
NRRL B-12329—*E. coli* RR1 (pUC1026)
NRRL B-12330—*E. coli* RR1 (pUC1027)
NRRL B-12186—*E. coli* RR1
NRRL B-12328—*E. coli* GM119

These deposits are available to the public upon the grant of a patent to the assignee, The Upjohn Company, disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

Figure 1:
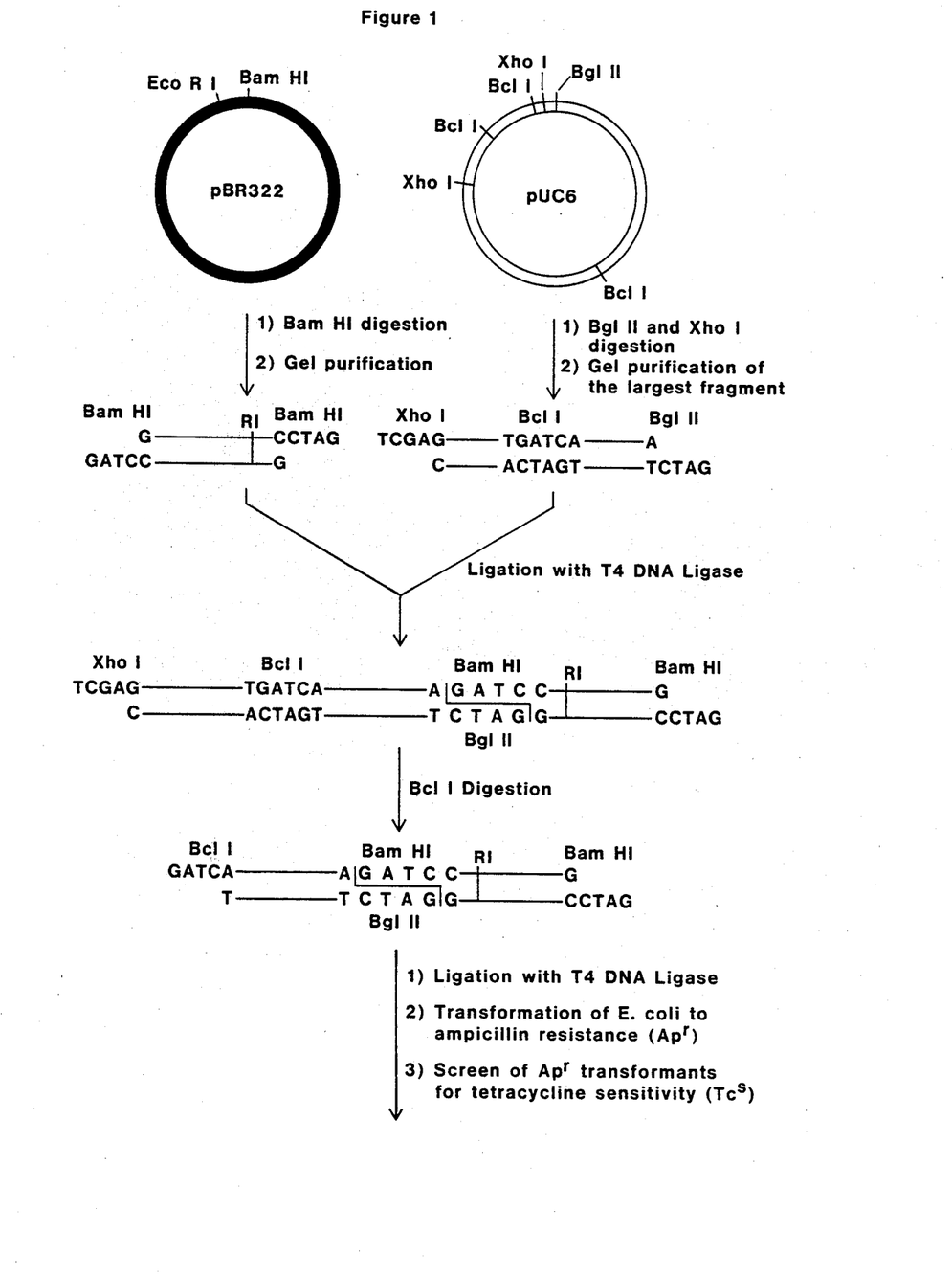
FIG. 1—Construction of recombinant plasmid pUC1026.
Figure 2:
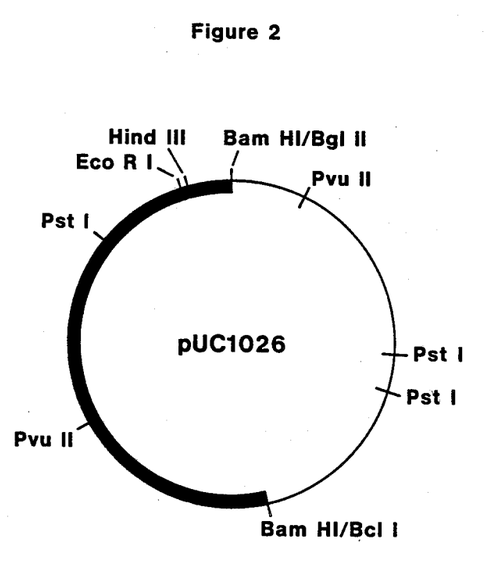
FIG. 2—Restriction endonuclease cleavage map for plasmid pUC1026.
Figure 5:
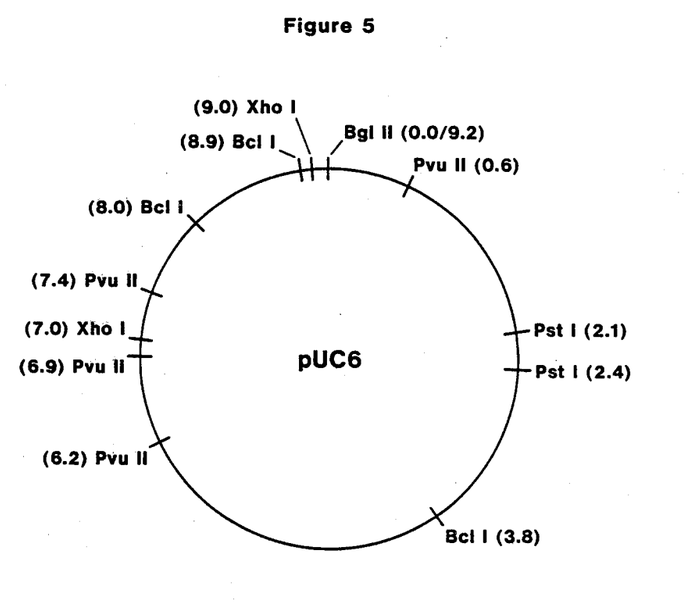
FIG. 5—Restriction endonuclease cleavage map for plasmid pUC6.

Plasmid pUC1026 was constructed as follows: (1) The *E. coli* vector plasmid pBR322 was digested with endonuclease BamHI and the linear plasmid DNA purified by agarose gel electrophoresis; (2) The *S. espinosus* plasmid pUC6 was digested with endonucleases BglII and XhoI and the largest restriction fragment was purified by agarose gel electrophoresis; (3) The purified DNA's from (1) and (2) were ethanol precipitated and ligated with T4 DNA ligase. [The only ligations that will occur are between BamHI and/or BglII cleavage site ends because XhoI ends will not pair with either BamHI or BglII ends. Hence, this process optimizes recombinant molecule formation]; (4) The ligated sample was then deproteinized by phenol extraction and digested with endonuclease BclI; (5) Again the sample was deproteinized by phenol extraction and then ligated with T4 DNA ligase; (6) Finally, the ligated sample was ethanol precipitated and used to transform *E. coli* culture RR1 to ampicillin resistance (Ap$^r$). Ap$^r$ colonies were screened for tetracycline sensitivity which is a phenotype indicative of cloning of DNA into the pBR322 BamHI site. In the construction of pUC1026, we have cloned the DNA sequences spanning the coordinates 0.0–3.8 kb in the pUC6 genome (FIG. 5). In particular, the orientation of the cloned sequence in pBR322 is as shown in FIG. 2.

By comparison, plasmid pUC1027 was constructed in the following manner. (1) The pUC6:pBR322 cointegrate plasmid pUC1013 was transferred to an *E. coli* host (GM 119) which doesn't methylate endonuclease BclI restriction sites and thereby leaves them available to BclI cleavage. Plasmid pUC1013 was then isolated from this host; (2) The pUC1013 DNA from (1) was digested with endonuclease BclI and the largest DNA fragment was purified by agarose gel electrophoresis;

(3) This fragment was ligated with T4 DNA ligase and used to transform *E. coli* host RR1 to ampicillin resistance. In the construction of plasmid pUC1027, the pUC6 sequences between 3.8 and 8.9 kb (FIG. 5) were deleted from pUC1013.

A part of the utility of pUC1026 and pUC1027 is that they consist of DNA sequences from very different bacterial hosts, i.e. hosts that have not been shown capable of exchanging genetic information by normal physiological means. As such, pUC1026 and pUC1027 can function as vectors into both of these organisms (i.e. *E. coli* and Streptomyces). Clearly, pUC1026 and pUC1027 can replicate and be maintained as autonomous plasmids in *E. coli*. They may also replicate and be maintained autonomously in various Streptomyces species. Plasmids pUC1026 and pUC1027 may also be used as recombinant DNA vectors in conjunction with pUC6 to transform Streptomyces; whereby, in vivo recombination between pUC6 and a recombinant derivative of pUC1026 or pUC1027 can give rise to a stable nonchromosomal gene system in the recipient streptomycete.

As a vector, pUC1026 contains single sites for endonucleases EcoRI and HindIII. Plasmid pUC1026 can readily be obtained from various *E. coli* hosts and will exhibit replication in the presence of chloramphenicol. Plasmid pUC1026 has a molecular weight of ~$5.4 \times 10^6$ daltons. By comparison, plasmid pUC1027 has single cleavage sites for endonucleases EcoRI, HindIII, XhoI and BclI. The XhoI site can function in cloning both XhoI and SalI digested DNA. The BclI site can function in cloning BclI, BamHI, BglII, MboI or Sau3A digested DNA. Plasmid pUC1027 can also be isolated from various *E. coli* hosts and replicates in the presence of chloramphenicol. The molecular weight of pUC1027 is ~$5.6 \times 10^6$ daltons.

Figure 6:
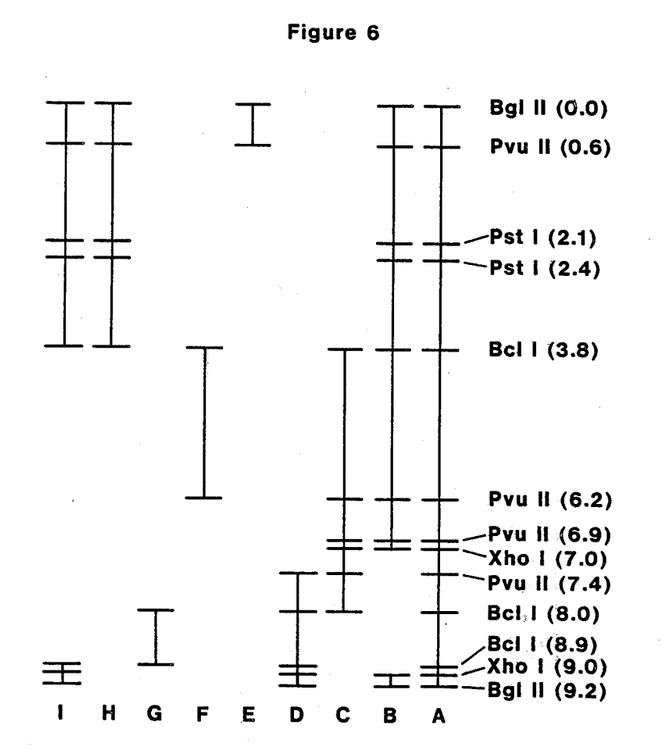
FIG. 6—Linear restriction endonuclease cleavabe map of plasmid pUC6 DNA sequences cloned into plasmid pBR322.

The plasmids pUC1026 and pUC1027 are unique in that they do not contain the pUC6 sequences mapping between 3.8 and 6.2 kb on the pUC6 map (FIGS. 5 and 6). This region of the pUC6 genome contains a genetic locus which causes pUC6:pBR322 recombinant plasmids to be unstable in *E. coli* hosts. FIG. 6 shows the genomic composition of several pBR322:pUC6 recombinant plasmids and indicates which portions of the pUC6 genome they contain. Table 1 compares the stability of these plasmids in *E. coli* hosts. Only those plasmids containing the 3.8–6.2 kb region of pUC6 are unstable. The relative amount of pUC6 DNA in these recombinants cannot account for this phenomenon. Thus, the deletion or omission of the 3.8–6.2 kb region of pUC6 from recombinant plasmids makes those recombinant plasmids more stable in hosts which are naive to the existence of the pUC6 genome. This, combined with recombinant DNA manipulations (e.g. those described for the construction of pUC1026 and pUC1027), constitutes a process whereby stable recombinant plasmids can be generated between plasmids from different organisms (e.g. *E. coli* and Streptomyces).

The following examples are illustrative of the process and products of the subject invention but are not to be construed as limiting. All percentages are by weight and all solvent mixture proportions are by volume unless otherwise noted.

EXAMPLE 1

Isolation of Vector pBR322 DNA from *E. coli* NRRL B-12014

A 100 ml. culture of *E. coli* RR1 (pBR322) is grown overnight in L-broth which consists of the following ingredients:

Bacto tryptone (Difco): 10 g./liter
Bacto yeast extract (Difco): 5 g./liter
NaCl: 5 g./liter
Ampicillin: 50 mg./liter The cells are recovered by centrifugation at 17,000×g. for 10 minutes in a refrigerated centrifuge. The pellet is suspended in 2.5 ml. 50 mM tris buffer (pH 8) containing 25% sucrose. One-half ml. of lysozyme stock solution is added (5 mg./ml. in TES buffer). The mixture is allowed to stand in ice for 5 minutes. At this point 1 ml. EDTA (02.5 M, pH 8) is added and the mixture is again allowed to stand in ice for 5 minutes. One and a quarter ml. of 5 M NaCl and 1 ml. 10% SDS (sodium dodecyl sulfate) are then added. The mixture is shaken on a Vortex and incubated at 37° C. for 20 minutes. Then 10 μl of ribonuclease (20 mg./ml.) is added and the sample is again incubated at 37° C. for 20 minutes. The mixture is then kept in ice overnight and then centrifuged at 35,000×g. for 30 minutes in a refrigerated centrifuge. 2 ml. of the supernatant solution (lysate) are carefully removed with a pipette. Four and one-half ml. of TES buffer (30 mM tris.HCl, pH 8, 5 mM EDTA.Na$_2$, 50 mM NaCl) are mixed with 1.5 ml. EtBr (ethidium bromide) stock (1 mg./ml. in TES buffer) and 7.5 g. solid CsCl. After the salt has dissolved, 2 ml. of the lysate, described above, is added and the mixture is transferred into a polyallomer tube fitting a titanium 50 (50 Ti) head (Beckman ultracentrifuge). The tubes are filled to the top with mineral oil and centrifuged in a Beckman ultracentrifuge at 40,000 rpm in a 50 Ti head at 15° C. for at least 2 days. The DNA is located under a long wave UV-lamp and the heavier band containing the plasmid DNA is removed with a syringe by puncturing the tube wall from the side. The samples are extensively dialyzed against 200 volumes of TES buffer at 4° C. Following dialysis, 1/10 sample volume of a 3 M NaAcetate stock solution is added and the plasmid DNA is precipitated by the addition of 2 volumes of cold ethanol. The resulting pellet is then lyophilized and redissolved in 200 μl 10 mM tris buffer, pH 7.8 containing 1 mM EDTA.Na$_2$ and frozen for storage.

EXAMPLE 2

Isolation of Plasmid pUC6 from a Biologically Pure Culture of Streptomyces espinosus, biotype 23724a, NRRL 11439

The spores from a biologically pure culture of *Streptomyces espinosus* biotype 23724a, NRRL 11,439, are inoculated into 10 ml. of the following Difco Antibiotic Medium No. 3 Broth (Difco Labs., Detroit, Mich.): 0.15% Beef extract; 0.15% yeast extract; 0.5% peptone; 0.1% glucose; 0.35% NaCl; B 0.368% K$_2$HPO$_4$; 0.132% KH$_2$PO$_4$.

The medium has previously been sterilized in a 50 ml. Erlenmeyer flask. After inoculation, the flask is incubated at 37° C. for about 36 to 48 hours on a Gump or New Brunswick rotary shaker operating at 100–250 rpm. Upon completion of the incubation, the mycelia-broth suspension in the flasks is homogenized under sterile conditions and is then mixed in a sterile 125 ml. Erlenmeyer flask containing 10 ml. of the above medium and also, advantageously 68% (w/v) sucrose and 1% (w/v) glycine. The addition of sucrose and glycine facilitates the subsequent lysing of the cells. The amounts of sucrose and glycine in the medium can be varied by routine adjustments with the goal being to facilitate the subsequent lysing of the cells. The flask is then incubated further for another 36 to 48 hours at 37° C. on a Gump rotary shaker, as above. After this incubation, the mycelia are separated from the broth by low speed centrifugation, for example, at 6000×g. for 15 minutes at 4° C. and decantation of the supernatant from the mycelial pellet.

The supernatant is discarded and the pellet is resuspended in 1.5 ml. of an isotonic buffer containing ethylenediaminotetraacetic acid (EDTA) and sucrose, e.g., TES buffer [0.03 M tris(hydroxymethyl)aminomethane (Tris), 0.005 M EDTA and 0.05 M NaCl; pH=8.0] containing 20% (w/v) sucrose. Next, 1.5 ml. of a 5 mg./ml. solution of lysozyme in the same buffer is added and the mixture is incubated at 37° C. for 30 minutes with occasional mixing. Then, 1.5 ml. of 0.25 M EDTA (pH=8.0) is added and this mixture is incubated 15 minutes at 37° C. Subsequently, the cell suspension is lysed by the addition of 2.5 ml. of a lytic mixture, e.g. [1.0% (w/v) Brij-58 (a detergent sold by Pierce Chem. Co., Rockford, Ill.), 0.4% (w/v) deoxycholic acid, 0.05 M Tris (pH=8.0) and 0.06 M EDTA] and incubation of this mixture at 37° C. for 20 minutes. The lysate is then sheared by passing it 5-10 times through a 10 ml. pipette. The sheared lysate is then digested with ribonuclease (140 μg/ml.) and pronase (300 μg/ml.) for an additional 20 minutes at 37° C. Alternatively, the cell-lysozyme-EDTA mixture can be digested with ribonuclease and pronase before lysis with a lytic agent such as 2% sodium dodecyl sulfate in water.

This crude lysate material is then mixed with a salt, for example, cesium chloride (preferred), and cesium sulfate, and the intercalating dye ethidium bromide to give a solution of density $\rho=1.550$. This solution is centrifuged to equilibrium at 145,000×g. (isopyonic density gradient centrifugation). The covalently closed circular plasmid DNA is then visible in the centrifuge tube under long wave ultraviolet (320 nm) illumination as a faint fluorescent band below the intensely fluorescent band of linear chromsomal and plasmid DNA's.

Covalently closed circular plasmid DNA is prepared for characterization by removing it from the isopycnic gradients, extracting the ethidium bromide by two treatments with one-third volume of isopropyl alcohol and then dialyzing the aqueous phase against an appropriate buffer, e.g., 0.1×SSC buffer (0.015 M NaCl, 0.0015 M sodium citrate; pH=7.4) to yield essentially pure pUC6.

Characteristics of pUC6

Molecular Weight: ca. 6.0 megadaltons
Copies per Cell: 20-40
Restriction Endonuclease Sensitivities: pUC6 has the following sensitivities to restriction endonucleases.

| Plasmid Sensitivities to Restriction Endonucleases | | | |
|---|---|---|---|
| | # Cleavage Sites | | # Cleavage Sites |
| Enzyme | pUC6 | Enzyme | pUC6 |
| BglI | >7 | BglII | 1 |
| BamHI | 0 | HpaI | 0 |
| HpaII | Many | HindIII | 0 |
| EcoRI | 0 | KpnI | 0 |
| PstI | 0 (2)* | PvuII | 4 |
| MboII | >5 | AvaI | >7 |
| XbaI | 0 | XhoI | 2 |
| SalI | 5-6 | SmaI | >5 |
| HincII | >7 | BclI | 3 |

*Plasmid pUC6 DNA isolated from *Streptomyces espinosus* NRRL 11439 is not cleaved by PstI. However, when pUC6 is cloned into *E. coli* K12, or a derivative thereof, two PstI cleavage sites can be detected. This indicates PstI sites are modified in *S. espinosus* NRRL 11439.

These results were obtained by digestion of pUC6 DNA in the presence of an excess of restriction endonuclease. The number of restriction sites were determined from the number of resolvable fragments in either 0.7 or 1.0% agarose gels.

EXAMPLE 3

Isolation of Plasmid pUC1013 From NRRL B-12107—*E. coli* CSH50 (pUC1013)

Figure 3:
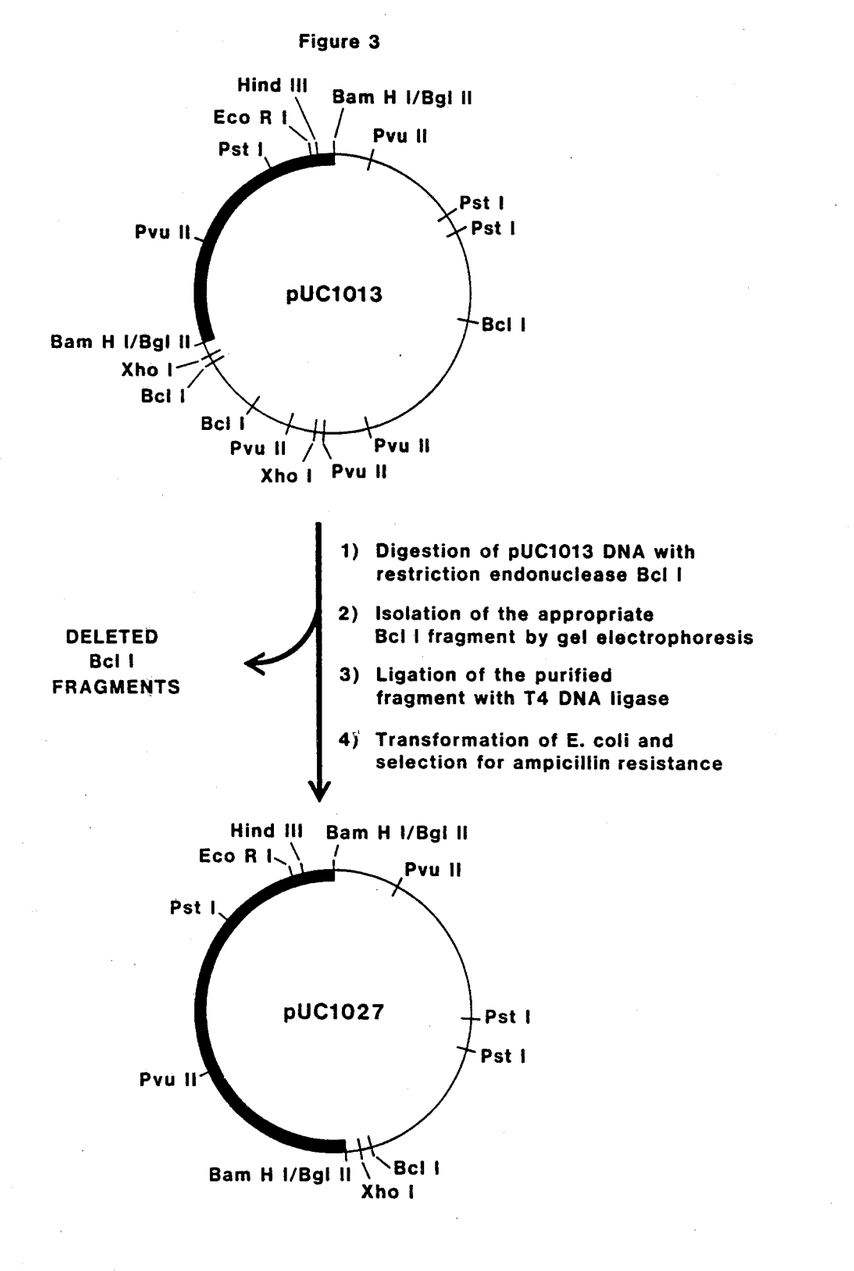
FIG. 3—Construction of recombinant plasmid pUC1027.
Figure 4:
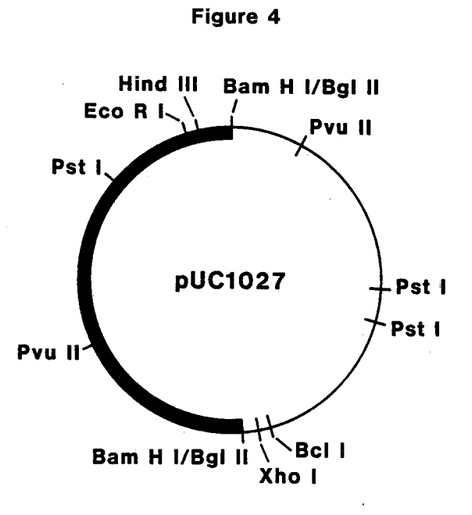
FIG. 4—Restriction endonuclease cleavage map for plasmid pUC1027.

Plasmid pUC1013 can be isolated from its *E. coli* host by well known procedures, e.g., using the cleared lysate-isopycnic density gradient procedures. Once transformants containing pUC1013 are identified, they are separated as pure entities in a pure culture. This plasmid can be differentiated as a distinct entity by its unique restriction patterns as would be predicted by its restriction map (FIG. 3). Note: When plasmid pUC1013 is maintained in a DNA modification proficient host such as *E. coli* CSH50, the BclI restriction sites are modified such that they can not be detected by BclI digestion. However, maintenance of pUC1013 in an adenine methylase deficient host allows the demonstration of the presence of BclI restriction sites.

EXAMPLE 4

Preparation of Recombinant Plasmid pUC1026 and Transformation into *E. coli* RR1

Plasmids pUC6 and pBR322, prepared as described above, are linearized by digestion with restriction endonucleases BglII and XhoI for pUC6, and BamHI for pBR322. Plasmid pBR322 DNA is digested with BamHI restriction enzyme by mixing ~50 μl. of DNA (~0.5 μg) solution in TE buffer (0.01 M Tris.HCl, 0.001 M Na₂ EDTA; pH 8.0) with 50 μl of 2X restriction buffer (Post et al., Cell 15, 215-229, 1978) and 4 units of BamHI enzyme preparation. This mixture is incubated at 37° C. for 1 hour. The digest is then applied to a 1% preparative low melting point agarose gel and electrophoresed for ~3 hours at 50 volts and 4° C. The resolved DNA fragments are visualized by ethidium bromide staining and long wave ultraviolet light illumination. The region of the gel containing the DNA is excised from gel and heated to 65° C. in the presence of 1.5 ml. of TE buffer to melt the gel and release the DNA from the gel matrix. This suspension is chilled and centrifuged at 37,000×g to pellet the agarose. The supernatant is decanted and saved. The agarose pellet is extracted a second time with TE buffer. The two supernatants are pooled and ethanol precipitated by the addition of 0.1 volume of 3 M Na Acetate and 2 volumes 95% ethanol at −20° C. The DNA precipitate is collected by centrifugation at 85,000 ×g at 4° C. for 60 minutes. The precipitate is redissolved in 100 μl of TE buffer. This sample is used for ligation as described below.

Plasmid pUC6 is subjected to BglII and XhoI digestion. The BglII digestion takes place in a reaction mixture containing 50 μl of pUC6 DNA (~0.5 μg) solution in TE buffer and 50 μl of 2X BglII restriction buffer and 4 units of BglII enzyme. This mixture is incubated at 37° C. for one hour and the digest placed in and isolated from a preparative agarose gel electrophoresis system as described above.

The XhoI digestion is done as follows:

Approximately 0.5 μg of pUC6 DNA in 25 μl of TE buffer is mixed with an equal volume of 2X XhoI restriction enzyme buffer (0.3 M NaCl, 12 mM Tris.HCl [pH 7.4], 12 mM $MgCl_2$, 12 mM 2-mercaptoethanol) and two units of XhoI restriction enzyme. This sample is digested for one hour at 37° C.

The resulting digest is then applied to a 1% preparative low melting point agarose gel and electrophoresed for ~3 hours at 50 volts and 4° C. The remainder of the agarose gel procedure is as described above.

For ligation, 25 μl of BamHI digested pBR322 DNA, 25 μl of BglII and XhoI digested pUC6 DNA and 20 μl DD $H_2O$ are combined. Ten μl 100 mM DDT, 10 μl 50 mM $MgCl_2$ and 10 μl of 0.5 mM ATP are combined with the restricted DNA mixture. Finally, 1.0 u of $T_4$ DNA ligase is added and the sample is kept in ice for 1-2 days.

The ligated DNA sample is deproteinized by standard phenol extraction. An equal volume of 2X BclI reaction buffer [40 mM KCl, 12.0 mM Tris HCl (pH 8.0), 13.2 mM $MgCl_2$, 12 mM 2-mercaptoethanol] is added together with 1-2 units of BclI enzyme and the digestion conducted at 60° C. for 1 hour. Following this, the sample is again deproteinized by standard phenol extraction, and then ligated with T4 DNA ligase, as described above. The ligated sample is ethanol precipitated and used to transform $E.$ $coli$ culture RR1 to ampicillin resistance ($Ap^r$).

For transformation into $E.$ $coli$ RR1 inoculum is grown overnight in L-broth and diluted 1:100 into fresh L-broth the next day. The cells are incubated at 37° C. and allowed to grow to an $OD_{650}$ of 0.2. At this point 50 ml. of culture is centrifuged in the cold, the pellet resuspended in 20 ml. cold 100 mM $CaCl_2$, incubated at 0° C. for 20-25 minutes and centrifuged again. The pellet is then resuspended in 0.5 ml. cold 100 mM $CaCl_2$ solution and kept at 0°-4° C. for 24 hours. (Dagert, M. and Ehrlich, S. D. 1979, Gene 6: 23-28) One hundred μl of pUC1026 ligase mixture (see above) is mixed with 500 μl cell suspension. This mixture is kept in ice for 10 minutes, and then at 37° C. for 5 minutes. Ten to 20 ml. of L-broth is added and the cell suspension is incubated 1-2 hours at 37° C. Next, 100 μl aliquots are plated on freshly prepared agar plates containing 25 ml. of L-broth, 1.5% agar, and 50 μg of ampicillin/ml. Colonies are selected and scored for tetracycline sensitivity.

Suspected recombiant DNA containing transformants are then grown in 25 ml. cultures. Cleared lysates are prepared by pelleting the cells from the culture medium at ~10,000×g. The pellet is resuspended in 10 ml. of cold TES buffer (30 mM Tris.HCl, 5 mM $Na_2$ EDTA and 50 mM NaCl, pH 8.0) and pelleted again. This pellet is resuspended in 1 ml. of TES buffer containing 20% sucrose. 0.2 ml. of lysozyme solution (5 mg./ml. in TES) is added and incubated on ice 15 minutes at which time 0.4 ml. of 0.25 M $Na_2$ EDTA (pH 8.0) is added and the incubation continued 15 minutes. 1.6 ml. of a lytic mix (1% Brij 58, 0.4% Na deoxycholate, 0.05 M Tris.HCl, 62.5 mM $Na_2$ EDTA; pH 8.0) is added and the lysate incubated an additional 15 minutes at 4° C. The lysate is sheared by passage 5 times through a 10 ml. pipette. The bulk of the cellular DNA and debris are removed by centrifugation at 48,000×g for 30 minutes. The cleared lysate is digested successively for 15-minute intervals with pancreatic RNAse A (100 mcg./ml.) and Pronase (200 mcg./ml.) at 37° C. These lysates are then centrifuged in CsCl-ethidium bromide isopycnic density gradients. Plasmid DNA isolated from these gradients is characterized by digestion with restriction endonucleases.

EXAMPLE 5

Preparation of Recombinant Plasmid pUC1027 and Transformation into $E.$ $coli$ RR1

Plasmid pUC1013 can be obtained as described in Example 3. This plasmid is then transferred to $E.$ $coli$ (GM 119), NRRL B-12328, by the procedures disclosed in Example 4. Other well known procedures also can be used. Plasmid pUC1013 is then isolated from this host by standard procedures, e.g. see Examples 1-3. The pUC1013 DNA is then digested with BclI using the procedures disclosed in Example 4. The resulting largest DNA fragment is purified by agarose gel electrophoresis, also as described in Example 4. This fragment is then ligated with T4 DNA ligase and used to transform $E.$ $coli$ RR1 to ampicillin resistance. These procedures also are as described in Example 4.

Recombinant plasmids were characterized by cleavage with restriction endonucleases.

Restriction endonucleases were obtained as commercial preparations from Miles Laboratories, Bethesda Research Laboratories and New England Biolabs. Enzyme digestions were prepared in accordance with the conditions specified by the suppliers using at least a two-fold excess of endonuclease.

The digested samples were applied to 0.7-1% agarose gels and were electrophoresed for 2 hours at a constant applied voltage of 10-15 v/cm of gel height. [Sharp, P. A., Sugden, J. and Sambrook, J. 1973. Detection of two restriction endonuclease activities in $Haemophilus$ $parainfluenzae$ using analytical agarose-ethidium bromide electrophoresis. Biochemistry 12, 3055-3063]. The molecular weight of restriction fragments were determined relative to the standard migration patterns of bacteriophage lambda DNA digested with enzyme HindIII [Murray, K. and Murray, N. E. 1975. "Phage Lambda receptor chromosomes for DNA fragments made with restriction endonuclease III of $Haemophilus$ $influenzae$ and restriction endonuclease I of $Escherichia$ $coli$." J. Mol. Biol. 98, 551-564] or EcoRI [Helling, R. B., Goodman, H. M. and Boyer, H. W. 1974. "Analysis of endonuclease R.EcoRI fragments of DNA from lambdoid bacteriophages and other viruses by agarose-gel electrophoresis." J. Virology 14, 1235-1244].

Recombinant plasmids pUC1026 and pUC1027 can be isolated from their $E.$ $coli$ hosts by well known procedures, e.g., using the cleared lysate-isopycnic density gradient procedures described above. Once transformants containing pUC1026 or pUC1027 are identified, they are separated as pure entities in a pure culture. These plasmids can be differentiated as distinct entities by their unique restriction patterns as would be predicted by their restriction maps.

Examples of other vectors which can be used in the invention as a substitute for pBR322 are pBR313, which codes for ampicillin and tetracycline resistance, pBR325, which codes for ampicillin, tetracycline and chloramphenicol resistance, pSC101, which codes for tetracycline resistance, pCR11, which codes for kanamycin resistance, λ bacteriophage vectors, for example, charon phages, and yeast 2μ plasmid DNA.

Examples of other hosts for the vectors are any E. coli K-12 derivative [Bacteriological Reviews, Dec. 1972, pages 525–557] (these are listed as approved hosts in the NIH Guidelines) and yeasts, other fungi, or other bacteria. It is recognized that these latter hosts would also have to fill the criteria for approved hosts as described in the NIH Guidelines.

TABLE 1

Stability of Plasmid Born Ampicillin Resistance in the Absence of Antibiotic Selection

| Plasmid[b] | Percent Ap[r] Clones in Absence of Selection[a] | | | | | | | |
|---|---|---|---|---|---|---|---|---|
| | Days at 28° C.[c] | | | | Days at 37° C.[c] | | | |
| | 1 | 2 | 3 | 4 | 1 | 2 | 3 | 4 |
| A | 51 | 51 | 51 | 50 | 28 | 18 | 12 | 4 |
| B | 51 | 51 | 54 | 52 | 44 | 39 | 39 | 32 |
| C | 26 | 44 | 27 | 35 | 61 | 43 | 52 | 42 |
| D | 100 | 100 | 100 | 100 | 100 | 100 | 100 | 100 |
| E | 100 | 100 | 100 | 100 | 100 | 100 | 100 | 100 |
| F[d] | 32 | 11 | 3 | 1 | 0 | 0 | 0 | 0 |
| G | 100 | 100 | 100 | 100 | 100 | 100 | 100 | 100 |
| H | 100 | 100 | 100 | 100 | 100 | 100 | 100 | 100 |
| I | 100 | 100 | 100 | 100 | 100 | 100 | 100 | 100 |

TABLE 1-continued

Stability of Plasmid Born Ampicillin Resistance in the Absence of Antibiotic Selection

| Plasmid[b] | Percent Ap[r] Clones in Absence of Selection[a] | | | | | | | |
|---|---|---|---|---|---|---|---|---|
| | Days at 28° C.[c] | | | | Days at 37° C.[c] | | | |
| | 1 | 2 | 3 | 4 | 1 | 2 | 3 | 4 |
| pBR322 | 100 | 100 | 100 | 100 | 100 | 100 | 100 | 100 |

[a]Single colonies of E. coli containing the various plasmids were selected from Difco Antibiotic Medium #3 (AB3) agar plates containing 40 mcg/ml ampicillin. These plates had been incubated at 28° C. for 24 hours. The single colonies were dispersed in 2–3 mls of AB3 broth, diluted in the same and plated on AB3 agar plates lacking antibiotic. These plates were incubated overnight at 28° C. or 37° C. Similarly, the AB3 broth containing the resuspended colony was split and incubated with aeration at both temperatures. On the following day, 100 random colonies from the AB3 agar plates were picked to AB3 agar containing 40 mcg/ml ampicillin. These plates were incubated at the appropriate temperature overnight and then examined for the number of ampicillin resistant (Ap[r]) clones. The overnight AB3 broth cultures were diluted 1:50 into fresh broth and the incubations continued at the appropriate temperatures. A sample of each overnight culture was also diluted and plated on AB3 agar at the appropriate temperature. These were handled as those plated on the first day. This process was repeated until four sets of data at each temperature were obtained.
[b]E. coli host RR1 was used in these experiments. Similar results were obtained with other E. coli hosts. Plasmids A-I are pBR322 derivatives containing the regions of pUC6 indicated in FIG. 6.
[c]The numerical values represent the number of Ap[r] clones among 100 random clones from nonselective medium.
[d]This plasmid cannot be maintained in an E. coli host of 37° C. even in the presence of antibiotic selection.

As is readily evident from the data in Table I, when considered with FIG. 6 of the drawings, the 2.4 kb pUC6 fragment between the PvuII site at 6.2 kb and the BclI site at 3.8 kb encodes a locus which causes instability of pUC6:pBR322 recombinant plasmids. If this locus is deleted, the pUC6:pBR322 recombinant plasmids become stable in the E. coli host. The criterion of stability of the vector in the host is of utmost importance for the utility of the vector. We expect it to be necessary to identify and map regions causing instability for any dual vector system when the components of that system are from hosts not normally considered to exchange genetic information. This constitutes a process important in the ultimate success of the dual or broad host range vector system.

The work described herein was all done in conformity with physical and biological containment requirements specified in the NIH Guidelines.

We claim:

1. A process for stabilizing an unstable dual plasmid comprising the genomes of plasmids pBR322 and pUC6 which comprises deleting a region identified as located within the 2.4 kb pUC6 fragment between the Pvu II site at 6.2 kb and the Bcl 1 site at 3.8 kb.

* * * * *

UNITED STATES PATENT OFFICE
CERTIFICATE OF CORRECTION

Patent No. 4,401,761                    Dated August 30, 1983

Inventor(s) Jack J. Manis and Sarah K. Highlander

It is certified that error appears in the above-identified patent and that said Letters Patent are hereby corrected as shown below:

Column 1, line 20 "described" should read --detected--.
Column 2, line 8 "mycleium" should read --mycelium--.
Column 2, line 56 "cleavabe" should read --cleavage--.
Column 2, line 59 "bases" should read --basis--.
Column 6, line 21 "(02.5 M" should read --(0.25 M--.
Column 6, line 63 "B 0.368%" should read --0.368%--.

Signed and Sealed this

Seventh Day of February 1984

[SEAL]

Attest:

GERALD J. MOSSINGHOFF

Attesting Officer        Commissioner of Patents and Trademarks